Oct. 28, 1958 R. S. MOORE Plant Pat. 1,766

MINIATURE ROSE PLANT

Filed Dec. 23, 1957

WITNESS

Addison E Avery

INVENTOR

Ralph S. Moore

Webster & Webster

ATTYS.

United States Patent Office

Plant Pat. 1,766

Patented Oct. 28, 1958

1,766

MINIATURE ROSE PLANT

Ralph S. Moore, Visalia, Calif.

Application December 23, 1957, Serial No. 704,850

1 Claim. (Cl. 47—61)

This invention relates to a new and distinct variety of miniature rose plant of hardy, dwarf, bush type, and which plant bears very attractive pink flowers.

I originated the instant variety of miniature rose plant in my nursery at Visalia, California, as a cross between an unnamed seedling (Rosa Wichuriana × Floradora) as the seed parent, and Oakington Ruby as the pollen parent; both of such parents being unpatented varieties.

Subsequent to the origination by me of the herein claimed variety of miniature rose plant, and when it came into maturity and its distinctive features were recognized, I successfully asexually reproduced said variety—in my nursery located as aforesaid—by cuttings; such reproductions having been found, by careful observation, to run true in all respects.

The present variety of miniature rose plant is particularly characterized by a plant which is very bushy, with all bright green twigs and stems; the plant branching freely from very close to soil level, and matures into a rounded bush about 10″ to 12″ high and 12″ in breadth. The foliage of the plant is very small, and a glossy or satiny green.

A further characteristic of the present variety of miniature rose plant resides in the ability to easily propagate such variety, both from hard wood and soft wood cuttings.

Additionally, the flowers—as the same open—are of a form similar to the Patty Lou miniature rose plant (United States Plant Patent No. 1,335). After the second or third day all of the petals have rolled backward lengthwise thereof, giving the effect of a miniature hybrid cactus dahlia; the petals rolling to lock almost tubular, with pointed tips. Also, the flowers have the over-all effect of being a clearer pink than most miniature rose plants which bear pink flowers, and all of the petals drop free while yet pink, giving a very clean and neat appearance.

As compared to the pollen parent, Oakington Ruby, the present variety is of lesser size in the mature plant, with smaller and brighter green leaves.

Figure 2:
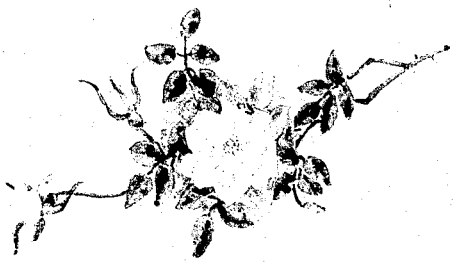
Fig. 2 is an elevation of a single stem illustrating a flower and buds.
Figure 1:
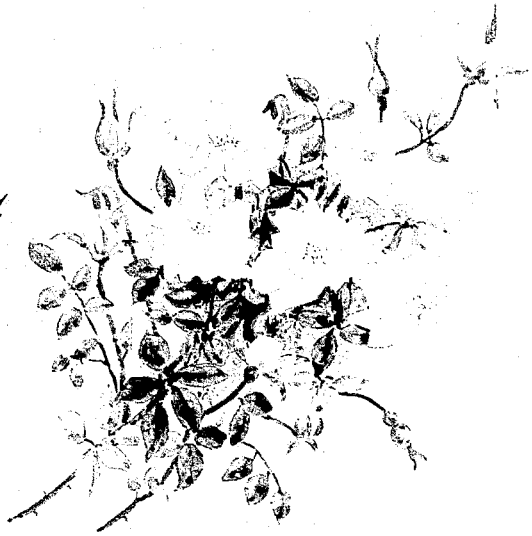
Fig. 1 shows a spray, including foliage, buds, and flowers.
Figure 3:
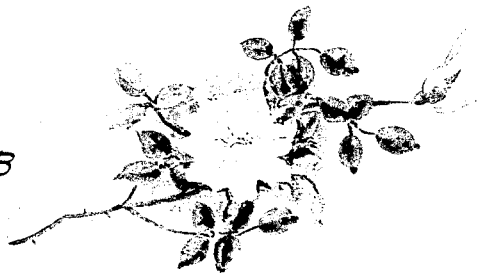
Fig. 3 is a similar view.

Referring now specifically to the new and distinct variety of miniature rose plant, the following is a detailed description thereof in outline; all major color plate identifications by Maerz and Paul Dictionary of Color, except where common terms of color definition are employed.

Type: Bush; dwarf; hardy; outdoors; seedling; cut flowers; garden decoration; potted plant.
Class: Miniature.

*Flowers*

Continuity: Continuous.
Fragrance: Slight.

Flowers Borne: Singly, or several (two to three) in irregular cluster on normal short stems.
Quantity of Bloom: Free.
Bud:
- *Peduncle.*—Medium length; slender; erect; almost smooth. Color—medium green.
- *Before calyx breaks.*—Size—small. Form—Short; globular, with foliaceous parts extending beyond the tip of the bud equal to one-half or more of its length. Color—medium green (20–L–7).
- *As calyx breaks.*—Color—rose pink (1–K–4).
- *As first petal opens.*—Size—small. Form—globular. Color—pink.

Bloom:
- *Size when fully open.*—Very small—averaging one inch.
- *Petalage.*—Very double, with from fifty or more petals, arranged regularly.
- *Form.*—Full. Petals first loosely rolled outwardly, becoming later fully rolled outwardly to substantially tubular, with pointed tips.

Petals: Medium thick; satiny, both sides.
- *Shape.*—Ovate.
- *Color.*—Light pink (1–N–1, shading darker to 1–E–4), shading toward white at the base of the petals, with pale green or citronelle (18–L–2) at the center of the flowers. The flowers tend to be a deeper pink in cool weather than they are in warm weather.
- *Behavior.*—Drops off cleanly.
- *Flower longevity.*—Bush in garden—three to four days. Cut flowers at normal room temperatures —one to two days.

*Reproductive organs*

Stamens: Few, mixed with petaloids.
Filaments: Short; white.
Anthers: Very small. Color—yellow (9–L–3).
Pollen: Very sparse.
Pistils: Few.
Styles: Uneven; short; bunched.
Stigma: White.
Ovaries: All enclosed in calyx.
Hips: None.
Sepals: Moderate length; spear shaped. Color—yellowish green.
Seeds: None.

*Plant*

Foliage:
- *Leaves.*—Compound of five leaflets; abundant; very small; glossy.
- *Leaflets.*—Ovoid; apex acute; margin serrate.
- *Rachis.* — Light. Upper side — smooth, grooved. Under side—sparsely thorny.
- *Stipules.*—Medium length; narrow, with moderately long points, turning out at an angle of less than 45 degrees.
- *Color.*—Top side—medium green (23–L–6). Under side—somewhat lighter green (21–J–6).

Growth:
- *Habit.*—Dwarf; bushy; much branched.
- *Growth.*—Vigorous; free.
- *Canes.*—Medium light.
- *Main stems.*—Color—bright green. Thorns—few to several; short; straight, with oval base. Prickles—none. Hairs—none.
- *Branches.*—Color—bright green. Thorns—none to few; short; straight. Prickles—none. Hairs—none.
- *New shoots.*—Color—bright green. Thorns—very few. Prickles—none. Hairs—none.

The miniature rose plant and its flowers as herein described may vary in slight detail due to climatic and soil conditions under which the variety may be grown.

The following is claimed:

A new and distinct variety of miniature rose plant of hardy, dwarf, bush type, substantially as described and illustrated, characterized by a small, bushy, much branched, rounded, vigorous growing plant having bright green twigs and stems, and very small, bright green, satiny foliage; a plant which propagates easily from both hard wood and soft wood cuttings; flowers similar to the Patty Lou when first open, but after the second or third day the petals roll backward lengthwise thereof to almost tubular, giving the effect of a miniature hybrid cactus dahlia; flowers which in over-all appearance are a clearer pink than most miniature roses; and petals which drop clean while yet pink; and further characterized—in comparison with the Oakington Ruby—by a plant of lesser size with smaller and brighter green leaves.

No references cited.